US010314658B2

(12) United States Patent
Gliner et al.

(10) Patent No.: US 10,314,658 B2
(45) Date of Patent: Jun. 11, 2019

(54) REGISTRATION OF AN ANATOMICAL IMAGE WITH A POSITION-TRACKING COORDINATE SYSTEM BASED ON VISUAL PROXIMITY TO BONE TISSUE

(71) Applicant: Biosense Webster (Israel) Ltd., Yokneam (IL)

(72) Inventors: Vadim Gliner, Haifa (IL); Ram Bernard Mayer, Raanana (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/493,618

(22) Filed: Apr. 21, 2017

(65) Prior Publication Data
US 2018/0303557 A1 Oct. 25, 2018

(51) Int. Cl.
*G06K 9/00* (2006.01)
*A61B 34/20* (2016.01)
(Continued)

(52) U.S. Cl.
CPC ............... *A61B 34/20* (2016.02); *A61B 5/06* (2013.01); *A61B 6/032* (2013.01); *A61B 6/501* (2013.01);
(Continued)

(58) Field of Classification Search
CPC ......... A61B 34/20; A61B 6/032; A61B 6/501; A61B 2034/2065; A61B 2090/365; A61B 2090/367; A61B 2090/3762; G06T 7/32; G06T 7/70; G06T 7/0012; G06T 2207/10081; A61M 25/0105; A61M 2025/0166
See application file for complete search history.

(56) References Cited

U.S. PATENT DOCUMENTS 5,391,199 A  2/1995  Ben-Haim
6,013,031 A  1/2000  Mendlein et al.
(Continued)

FOREIGN PATENT DOCUMENTS

WO  96/05768  2/1996
WO  2009147683 A1  12/2009
WO  2017030915 A1  2/2017

OTHER PUBLICATIONS

Extended European Search Report issued on Jul. 3, 2018 for the European Patent Application No. 18168416.8.
(Continued)

*Primary Examiner* — Shefali D Goradia
(74) *Attorney, Agent, or Firm* — Volpe and Koenig, P.C.

(57) ABSTRACT

A system and method for improving registration of an anatomical image with a position-tracking coordinate system based on visual proximity to bone tissue is presented. The method can comprise identifying, in a three-dimensional (3d) anatomical image of a patient organ, multiple anatomical points corresponding to respective predefined locations on a skin of the patient organ in a first coordinate system, performing initial registration of the first coordinate system and a second coordinate system by correlating between positions in the first coordinate system and respective anatomical points in the second coordinate system, viewing a position in the first coordinate system using a viewing device, when the position does not match a predetermined location, marking the position and weighting the position, and refining the initial registration of the first and second coordinate systems, by re-correlating between the positions, the marked positions and the respective anatomical points.

11 Claims, 3 Drawing Sheets

(51) Int. Cl.
- *A61B 5/06* (2006.01)
- *G06T 7/73* (2017.01)
- *G06T 7/32* (2017.01)
- *G06T 7/70* (2017.01)
- *A61B 6/03* (2006.01)
- *A61B 6/00* (2006.01)
- *A61M 25/01* (2006.01)
- *G06T 7/00* (2017.01)
- *A61B 90/00* (2016.01)

(52) U.S. Cl.
CPC ....... *A61M 25/0105* (2013.01); *G06T 7/0012* (2013.01); *G06T 7/32* (2017.01); *G06T 7/70* (2017.01); *G06T 7/73* (2017.01); *A61B 2034/2065* (2016.02); *A61B 2090/365* (2016.02); *A61B 2090/367* (2016.02); *A61B 2090/3762* (2016.02); *A61M 2025/0166* (2013.01); *G06T 2207/10068* (2013.01); *G06T 2207/10081* (2013.01); *G06T 2207/10088* (2013.01); *G06T 2207/30021* (2013.01)

(56) References Cited

U.S. PATENT DOCUMENTS

| | | | |
|---|---|---|---|
| 6,239,724 B1 | 5/2001 | Doron et al. | |
| 6,332,089 B1 | 12/2001 | Acker et al. | |
| 6,484,118 B1 | 11/2002 | Govari | |
| 6,560,354 B1 | 5/2003 | Maurer et al. | |
| 6,618,612 B1 | 9/2003 | Acker et al. | |
| 6,690,963 B2 | 2/2004 | Ben-Haim et al. | |
| 7,027,642 B2* | 4/2006 | Rubbert | A61C 7/00 382/154 |
| 8,821,376 B2* | 9/2014 | Tolkowsky | A61B 1/0052 600/101 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2008/0123923 A1 | 5/2008 | Gielen et al. | |
| 2010/0041949 A1* | 2/2010 | Tolkowsky | A61B 1/0052 600/109 |
| 2012/0155723 A1* | 6/2012 | Deno | G06T 7/0044 382/128 |
| 2014/0193053 A1* | 7/2014 | Kadoury | G06T 11/008 382/131 |
| 2014/0343408 A1* | 11/2014 | Tolkowsky | A61B 1/0052 600/424 |
| 2018/0308232 A1 | 10/2018 | Gliner | |

OTHER PUBLICATIONS

Sorger et al. "A novel platform for electromagnetic navigated ultrasound bronchoscopy (EBUS)," International Journal of Computer Assisted Radiology and Surgery, vol. 11, No. 8 (2015).

* cited by examiner

REGISTRATION OF AN ANATOMICAL IMAGE WITH A POSITION-TRACKING COORDINATE SYSTEM BASED ON VISUAL PROXIMITY TO BONE TISSUE

CROSS REFERENCE TO RELATED APPLICATIONS

This application incorporates by reference as if fully set forth U.S. application Ser. No. 15/493,703, titled "Registration of an Anatomical Image with a Position-Tracking Coordinate System Based on Proximity to Bone Tissue" filed on Apr. 21, 2017, the same date as the present application.

FIELD OF THE INVENTION

The present invention relates generally to registration of coordinate systems, and particularly to methods and systems for registering coordinate systems based on visual examination of a stationary organ.

SUMMARY OF THE INVENTION

A system and method for improving registration of an anatomical image with a position-tracking coordinate system based on visual proximity to bone tissue is presented. The method can comprise identifying, in a three-dimensional (3D) anatomical image of a patient organ, multiple anatomical points corresponding to respective predefined locations on a skin of the patient organ in a first coordinate system, performing initial registration of the first coordinate system and a second coordinate system by correlating between positions in the first coordinate system and respective anatomical points in the second coordinate system, viewing a position in the first coordinate system using a viewing device, when the position does not match a predetermined location, marking the position and weighting the position, and refining the initial registration of the first and second coordinate systems, by re-correlating between the positions, the marked positions and the respective anatomical points.

In one embodiment, the method can further comprise weighting the position, for example by creating multiple identical positions.

In one embodiment, the 3D anatomical image can comprise a computerized tomography (CT) anatomical image. In one embodiment, the patient organ comprises a patient head, and receiving the multiple positions comprises receiving positions located at the predefined locations on the patient head.

An apparatus for improving registration of an anatomical image with a position-tracking coordinate system based on visual proximity to bone tissue can comprise a medical device comprising a video display device, and a processor, which is configured to identify, in a three-dimensional (3D) anatomical image of a patient organ, multiple anatomical points corresponding to respective predefined locations on a skin or surface of the patient organ in a first coordinate system, perform initial registration of the first coordinate system and a second coordinate system by correlating between positions in the first coordinate system and respective anatomical points in the second coordinate system, view a position in the first coordinate system using a viewing device, when the position does not match a predetermined location, mark the position and weight the position, and refine the initial registration of the first and second coordinate systems, by re-correlating between the positions, the marked positions and the respective anatomical points.

In one embodiment, the processor is further configured to weight the position comprises creating multiple identical positions. In one embodiment, the medical device is a catheter and the video display device is a camera.

A computer program product for using proximal location sensors to improve accuracy and location immunity to interference is also presented.

The present invention will be more fully understood from the following detailed description of the embodiments thereof, taken together with the drawings in which:

DETAILED DESCRIPTION

Figure 1:
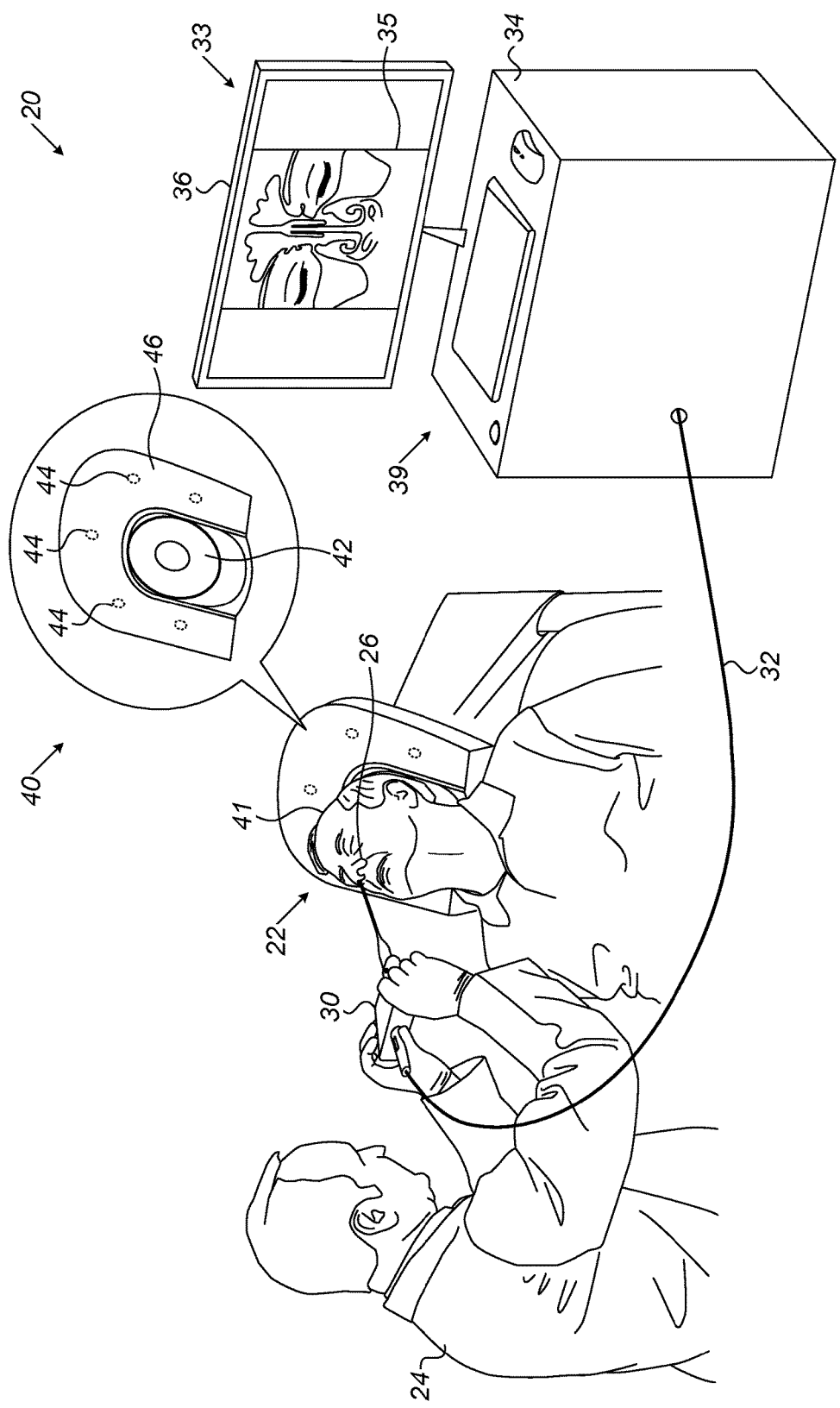
FIG. 1 is a schematic, pictorial illustration of a sinuplasty surgical system, in accordance with an embodiment of the present invention.

Some medical procedures, such as sinuplasty, may involve registration of an anatomical image of relevant organs with a coordinate system of a position tracking system. Using the registration, a surgical tool fitted with a position sensor may be navigated to the treated organs, and can be visualized overlaid on the anatomical image. In principle, pre-operative registration may be carried out using an external registration tool fitted with a position sensor of the position tracking system. Such a tool could be attached to preselected locations on the patient face (e.g., forehead, and centers of the two cheeks). The anatomical image may then be registered to the coordinate system of the position tracking system based on the measured positions of tissue at the preselected locations.

This possible solution, however, is likely to be inaccurate and unsuitable for sinuplasty procedures, in which it is typically important to obtain registration of the anatomical image at an accuracy level better than one mm. Since some facial elements may comprise soft tissue that deforms naturally, and because of the uncontrolled pressure applied on the tissue by the registration tool, the accuracy of this hypothetical solution may become unacceptable.

Embodiments of the present invention that are described below provide improved techniques for refining the initial registration between a coordinate system of an anatomical imaging system and a coordinate system of a position-tracking system. In the disclosed embodiments, an initial registration is performed in which a three-dimensional (3D) anatomical image of a patient head is acquired using a computerized tomography (CT) system. The anatomical image comprises anatomical points that are measured in a coordinate system of the CT, and should be mapped to a coordinate system of a position-tracking system.

In some embodiments, mapping between the two coordinate systems is carried out using a registration tool that comprises a position sensor of the position-tracking system. In order to perform the registration, a physician attaches the distal end of the registration tool to multiple predefined locations on a skin of the patient face. Examples of predefined locations can include, but are not limited to, cheeks, forehead, bridge of the nose, etc. At each of the predefined locations, the position tracking system measures the position of the position sensor (and thus of the predefined location) in its own coordinate system.

In some embodiments, the anatomical image is provided to a processor, which identifies the predefined locations in the anatomical image, and calculates (in the CT coordinate system) for each predefined location, a distance between the anatomical point corresponding to the predefined location and the closest point on a bone tissue of the patient face.

In some embodiments, the processor is configured to perform an initial registration of the coordinate systems of the CT to the position tracking systems, by correlating between the positions acquired by the registration tool and the respective anatomical points of the image acquired by the CT. In an embodiment, the processor carries out the initial registration using the respective weights, by applying a suitable registration method, such as the iterative closest point (ICP) method. The initial registration process typically estimates a transformation between the two coordinate systems, in which measurements at locations having a small distance to the closest bone tissue are given a high weight, and vice versa.

After the initial registration, a catheter comprising a sensor and a camera or other video display device can be inserted into the patient's cavity. Using this camera, the physician places the catheter on one of the predefined locations discussed above. For example, the physician places the catheter on the bridge of the nose as shown by the camera view. If the location displayed by the camera does not match the predefined location, the physician marks the camera-view location as the predetermined location. This camera-view location will be weighted in the registration calculations described in more detail below.

Due to their high accuracy, the disclosed techniques enable, for example, improved navigation of a sinuplasty surgical tool, which is inserted into the patient head and comprises another position sensor of the position-tracking system.

FIG. 1 is a schematic pictorial illustration of a magnetic position tracking system 20, in accordance with an embodiment of the present invention. System 20 is configured to track the position of one or more position sensors in the head of a patient 22. As will be described in detail hereinafter, the magnetic position tracking system 20 comprises magnetic field-generators and one or more position sensors. The position sensors generate position signals in response to sensed external magnetic fields from the field generators, thereby enabling a processor 34 to map the position of each sensor in the coordinate system of the position tracking system as will be described below.

Figure 2:
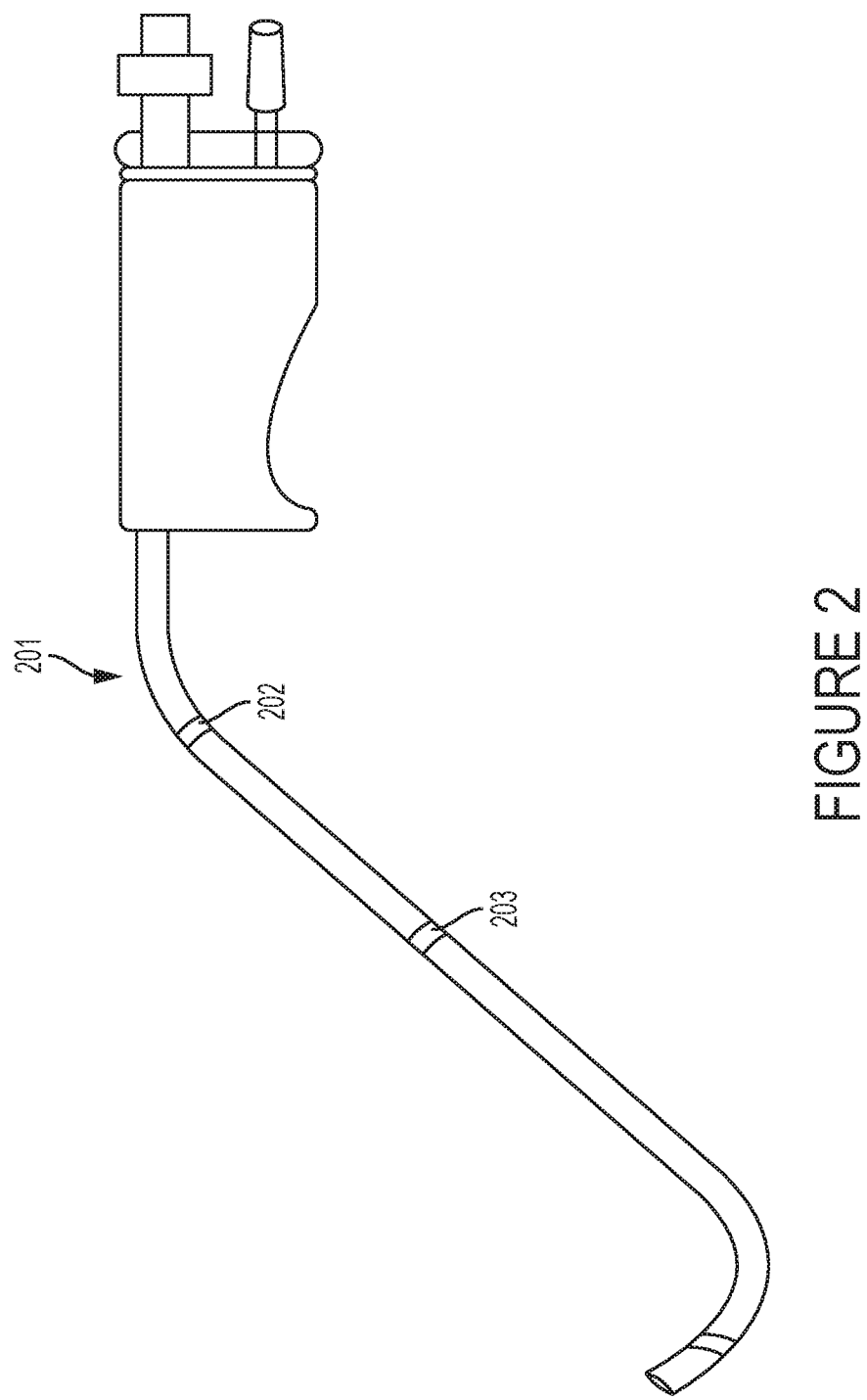
FIG. 2 is a schematic illustration of a medical device to be used with the surgical system in accordance with an embodiment of the present invention.

FIG. 2 is a schematic illustration of a medical device, such as a catheter, which can be used in the magnetic tracking system 20. The medical device 201 can include a video display element 202 as well as one or more sensors 203. Only one sensor is shown in FIG. 2 but more than one sensor can be provided on the medical device 201.

This method of position sensing is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Referring back to FIG. 1, in the present example, magnetic position tracking system 20 comprises a location pad 40, which comprises multiple field-generators 44 fixed on a frame 46. In the exemplary configuration shown in FIG. 1, pad 40 comprises five field-generators 44, but any other suitable number of generators 44 can be used. Pad 40 further comprises a pillow 42 placed under a head 41 of patient 22, such that generators 44 are located at fixed, known positions external to the patient. System 20 further comprises a console 33, which comprises a driver circuit (not shown) configured to drive field-generators 44 with suitable signals to generate magnetic fields in a predefined working volume around head 41. Location pad 40 is connected to the console 33 by a cable (not shown).

In some embodiments, magnetic position tracking system 20 comprises a registration tool 30, such as a handheld wand, which is used for registering the coordinate system of the magnetic position tracking system 20 with that of a pre-acquired computerized tomography (CT) image. The registration tool 30, which is used for the initial registration process, is configured to acquire position measurements.

Typically, a physician 24 performs the initial registration process. During this initial registration process, processor 34 is configured to calculate two coordinates for each predefined location on the patient head: 1) an "anatomical point" in a coordinate system of the CT system; and 2) a "position point" in a coordinate system of the position tracking system 20. The position point is derived from the position measurements of wand 30 at this predefined location, and is indicative of the coordinate of the skin at this location in the coordinate system of the magnetic position tracking system 20. The anatomical point is indicative of the coordinate of the skin at this location, as identified in the CT image. The processor 34 is configured to correlate between the anatomical points and the position points of the predefined locations in image 35, performing the initial registration process of registering the CT image with the coordinate system of the magnetic position tracking system 20. In some embodiments, the processor 34 is configured to register the coordinate systems of the CT to the position tracking systems, by correlating between the positions acquired by the registration tool and the respective anatomical points of the image acquired by the CT. In an embodiment, the processor 34 carries out the registration using the respective weights, by applying a suitable registration method, such as the iterative closest point (ICP) method. The registration process typically estimates a transformation between the two coordinate systems, in which measurements at locations having small distance to the closest bone tissue are given high weight, and vice versa.

The initial registration process is typically performed before the actual medical procedure, such as a sinuplasty procedure. During the medical procedure, physician 24 may insert into head 41 a medical device, such as a catheter 201 or other surgical tool, which comprises a camera 202 and/or other additional position sensors 203 of the magnetic position tracking system 20. Since the CT image is already registered with the position-tracking system, physician 24 may navigate the medical device 201 whose distal end is displayed on the CT image, to a target location in head 41. The medical device 201 is tracked in the position tracking system in accordance with its magnetic location, determined by one or more sensors 203 in the medical device, as well as the structures, e.g., physical features or elements in head 41 (and/or other cavity in which the medical device is inserted), displayed by the camera 202. In one embodiment, a target location may be a structure in head 41.

In alternative embodiments, instead of CT image 35, processor 34 is configured to receive one or more images acquired using another suitable anatomical imaging technique, such as fluoroscopy or magnetic resonance imaging (MRI), and to register these anatomical images with the coordinate system as described above.

In an embodiment, processor 34 is typically a computer comprising suitable front end and interface circuits for receiving data from external sources, as well as measurements from the position sensor of wand 30, via a cable 32, and video data from the camera 202, and for controlling other components of magnetic position tracking system 20. Console 33 further comprises input devices 39, such as a keyboard, mouse, microphone, gesture reading device or a touchscreen, and a display 36, which is configured to display the video data from the camera 131 as well as other data.

FIGS. 1 and 2 shows only elements related to the disclosed techniques, for the sake of simplicity and clarity. Magnetic position tracking system 20 typically comprises additional modules and elements that are not directly related to the disclosed techniques, and thus, these elements are intentionally omitted from FIG. 1 and from the corresponding description.

Processor 34 may be programmed in software to carry out the functions that are used by the system, and to store data in a memory (not shown) to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Figure 3:
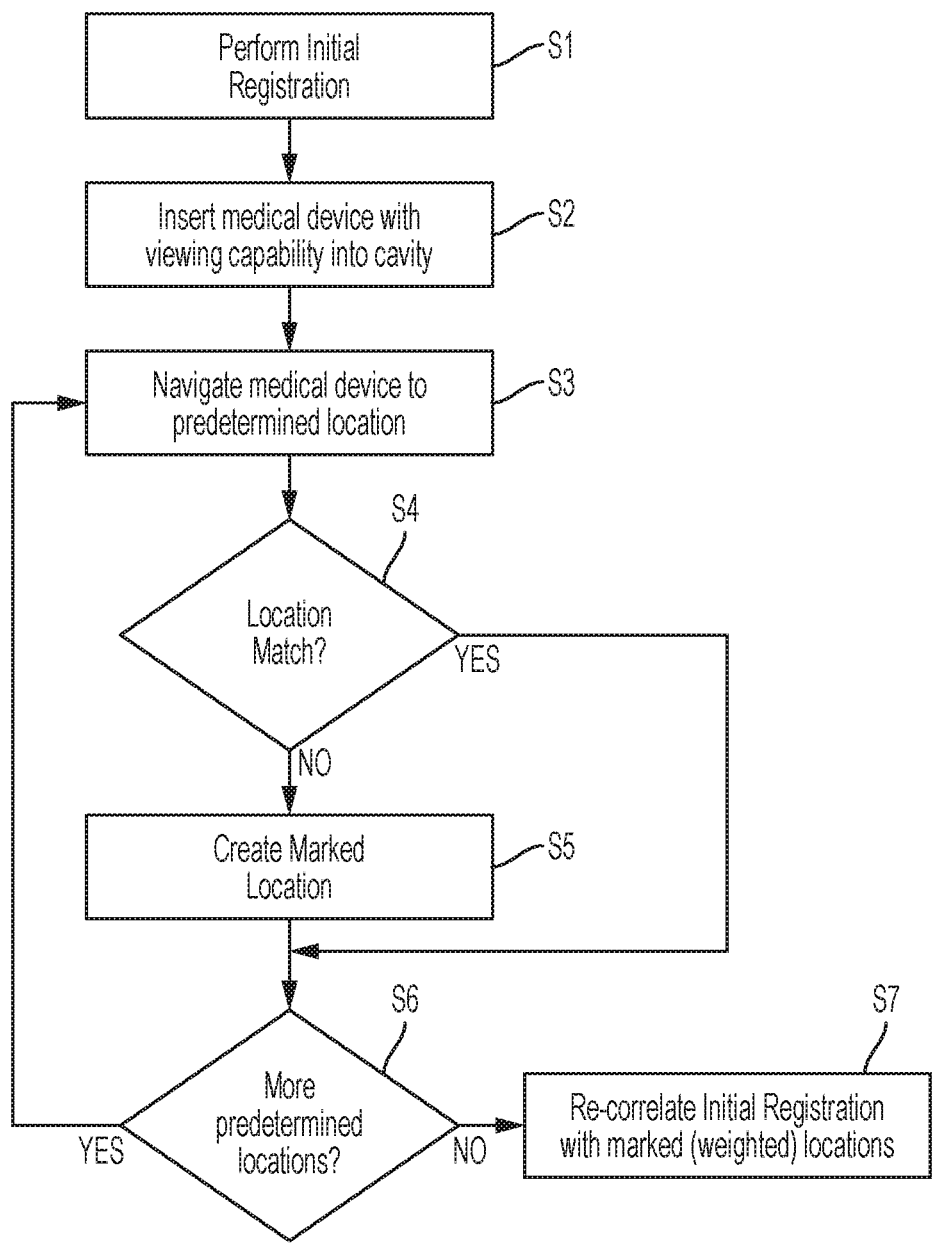
FIG. 3 is a flow chart that schematically illustrates a method for refining initial registration of a coordinate system of a magnetic position tracking system with that of a pre-acquired computerized tomography (CT) image, in accordance with an embodiment of the present invention.

FIG. 3 is a flow chart that schematically illustrates a method for improving an initial registration of the coordinate system of the magnetic position tracking system 20 with the coordinate system of a CT imaging system, in accordance with an embodiment of the present invention.

The method begins with the performance of an initial registration process in step S1. In one embodiment, the initial registration process can be the registration process described in the inventors' co-pending application entitled "Registration of an Anatomical Image with a Position-Tracking Coordinate System Based on Proximity to Bone Tissue" filed herewith, which is incorporated by reference as if fully set forth herein.

In step S2, insert a catheter 201 with viewing capability, e.g. having a camera 202, into a cavity of a patient.

In step S3, the catheter is navigated to a predetermined location in accordance with predetermined locations determined during initial registration. In one embodiment, the predetermined location is a structure in the cavity of the patient, such as, for example, a tip of the nose bone.

In step S4, it is determined whether the catheter location, as displayed by the camera, matches positional data at the predetermined location. If the locations match (S4=YES), go to step S6.

If the locations do not match (S4=NO), in step S5, a marked location, that is the location of the catheter 201 as shown by the camera 202, is created at the predetermined location.

In step S6, determine whether there are more predetermined locations to examine. If there are more predetermined locations to examine (S6=YES), go to step S3.

If all predetermined locations have been examined (S6=YES), in step S7 perform re-correlation to refine the initial registration by weighting location(s) marked in step S5.

In one embodiment, the initial registration is refined by performing calculations in which each marked location is duplicated multiple times. In one embodiment, each marked location can be duplicated one hundred times, for example. Accordingly, the marked locations are given significantly more weight than non-marked locations which had been determined in the initial registration process. Thus these weighted locations have higher impact on the refined registration than the weight at non-marked, predefined locations.

In an embodiment, processor 34 carries out the refined registration by applying a suitable method that iteratively minimizes the sum of distances between pairs of points of the CFOR and PFOR systems, such as the iterative closest point (ICP) method.

Although the embodiments described herein mainly address sinuplasty applications, the methods and systems described herein can also be used in other applications, such as in other Ear-Nose-Throat (ENT) applications and orthopedic applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. A method of registering coordinate systems, comprising:

identifying, in a first three-dimensional (3D) anatomical image of a portion of patient anatomy, multiple anatomical points in a first coordinate system corresponding to predetermined locations on a surface of the portion of patient anatomy;

identifying, in a second coordinate system of a position tracking system, position points corresponding to the predetermined locations on the surface of the portion of patient anatomy in a 3D space;

performing initial registration of the first coordinate system and the second coordinate system by correlating between the anatomical points in the first coordinate system and the position points in the second coordinate system;

displaying, using a viewing device of a medical tool inserted within the portion of patient anatomy, locations within the portion of the patient anatomy;

receiving, for each displayed location within the portion of the patient anatomy, indications of whether or not the displayed location matches one of the position points corresponding to the predetermined locations on the surface; and refining the initial registration of the first and second coordinate systems, by:

providing more weight to position points corresponding to displayed locations that do not match one of the position points than position points corresponding to displayed locations that do match one of the position points; and re-correlating between the anatomical points and the position points according to the weighted position points and the anatomical points such that the sum of distances between the correlated anatomical points and the position points is reduced.

2. The method according to claim 1, wherein:

providing more weight comprises iteratively duplicating the position points corresponding to displayed locations that do not match one of the position points at identical positions.

3. The method according to claim 1, wherein the 3D anatomical image comprises a computerized tomography (CT) anatomical image.

4. The method according to claim 1, wherein the portion of patient anatomy comprises a patient head, and the multiple anatomical points and the position points correspond to the predefined locations on the patient head.

5. An apparatus, comprising:

a display device; and a processor, which is configured to:

identify, in a first three-dimensional (3D) anatomical image of a portion of patient anatomy, multiple anatomical points in a first coordinate system corresponding to predetermined locations on a surface of the portion of patient anatomy;

identify, in a second coordinate system of a position tracking system, position points corresponding to the predetermined locations on the surface of the portion of patient anatomy in a 3D space;

perform initial registration of the first coordinate system and the second coordinate system by correlating between the anatomical points in the first coordinate system and the position points in the second coordinate system;

display on the display device, using a viewing device of a medical tool inserted within the portion of patient anatomy, locations within the portion of the patient anatomy;

receive, for each displayed location within the portion of the patient anatomy, indications of whether or not the displayed location matches one of the position points corresponding to the predetermined locations on the surface; and refining the initial registration of the first and second coordinate systems, by:

providing more weight to position points corresponding to displayed locations that do not match one of the position points than position points corresponding to displayed locations that do match one of the position points; and re-correlating between the anatomical points and the position points according to the weighted position points and the anatomical points such that the sum of distances between the correlated anatomical points and the position points is reduced.

6. The apparatus according to claim 5, wherein the processor is configured to:

provide more weight by iteratively duplicating the position points corresponding to displayed locations that do not match one of the position points at identical positions.

7. The apparatus according to claim 5, wherein the 3D anatomical image comprises a computerized tomography (CT) anatomical image.

8. The apparatus according to claim 5, wherein the portion of patient anatomy comprises a patient head, and multiple anatomical points and the position points correspond to the predefined locations on the patient head.

9. The apparatus according to claim 8, wherein the medical tool is a catheter and the video display device is a camera.

10. A non-transitory computer readable storage medium in which computer program instructions are stored, which instructions, when executed by a computer, cause the computer to perform steps of:

identifying, in a first three-dimensional (3D) anatomical image of a portion of patient anatomy, multiple anatomical points in a first coordinate system corresponding to predetermined locations on a surface of the portion of patient anatomy;

identifying, in a second coordinate system of a position tracking system, position points corresponding to the predetermined locations on the surface of the Portion of patient anatomy in a 3D space;

performing initial registration of the first coordinate system and the second coordinate system by correlating between the anatomical points in the first coordinate system and the position points in the second coordinate system;

displaying, using a viewing device of a medical tool inserted within the portion of patient anatomy, locations within the portion of the patient anatomy;

receive, for each displayed location within the portion of the patient anatomy, indications of whether or not the displayed location matches one of the position points corresponding to the predetermined locations on the surface; and refining the initial registration of the first and second coordinate systems, by:

providing more weight to position points corresponding to displayed locations that do not match one of the position points than position points corresponding to displayed locations that do match one of the position points; and re-correlating between the anatomical points and the position points according to the weighted position points and the anatomical points such that the sum of distances between the correlated anatomical points and the position points is reduced.

11. The computer readable storage medium according to claim 10, wherein:

providing more weight by iteratively duplicating the position points corresponding to displayed locations that do not match one of the position points at identical positions.

* * * * *